United States Patent [19]

O'Connell et al.

[11] Patent Number: 4,695,554

[45] Date of Patent: Sep. 22, 1987

[54] SAC OR LIPOSOME CONTAINING DYE (SULFORHODAMINE) FOR IMMUNOASSAY

[75] Inventors: James P. O'Connell, Chapel Hill, N.C.; Uri Piran, Norwood, Mass.; Daniel B. Wagner, Raleigh, N.C.

[73] Assignee: Becton Dickinson and Company, Franklin Lakes, N.J.

[21] Appl. No.: 716,533

[22] Filed: Mar. 27, 1985

Related U.S. Application Data

[63] Continuation-in-part of Ser. No. 579,667, Feb. 14, 1984, and a continuation-in-part of Ser. No. 650,200, Sep. 13, 1984.

[51] Int. Cl.$^4$ .................. G01N 33/533; B01J 13/02
[52] U.S. Cl. .................................... 436/528; 264/4.1; 264/4.3; 436/501; 436/536; 436/546; 436/800; 436/829

[58] Field of Search ............... 436/501, 537, 546, 800, 436/829, 536, 528; 264/4.1, 4.3

[56] References Cited

U.S. PATENT DOCUMENTS 4,372,745  2/1983  Mandle ............................ 436/537
4,605,630  8/1986  Kung ............................ 436/829 X

*Primary Examiner*—Sidney Marantz
*Attorney, Agent, or Firm*—Elliot M. Olstein

[57] ABSTRACT

A sac, in particular a vesicle, including as a detectable marker an absorbing dye having an extinction coefficient of at least 100,000 and a solubility in water of at least 0.1M; in particular, sulforhodamine B or salt thereof. The sacs have improved stability to leakage and are useful in a variety of assays; in particular, when sensitized with a ligand.

21 Claims, No Drawings

SAC OR LIPOSOME CONTAINING DYE (SULFORHODAMINE) FOR IMMUNOASSAY

This application is a Continuation-In-Part of U.S. Pat. application Ser. No. 06/579,667, filed on Feb. 14, 1984 and U.S. Pat. application Ser. No. 06/650,200 filed on Sept. 13, 1984.

This invention relates to sacs including a detectable marker, and the use thereof in an assay for an analyte. This invention further relates to sacs including a detectable marker which are sensitized with a ligand, and the use thereof in an assay for an analyte.

Sacs, and in particular, lipid vesicles, which include a detectable marker therein have been employed in assays for a ligand (analyte). In a representative assay, a ligand to be determined (analyte) and tracer comprised of a sac containing a detectable marker sensitized with the analyte or appropriate analog thereof compete for a limited number of binding sites on a binder for the analyte. The amount of tracer which becomes bound to the binder is inversely proportional to the amount of analyte in the sample. After separating bound and free tracer components, the amount of the bound and/or free tracer is ascertained by determining the detectable marker in the bound and/or free tracer portion of the sample, which provides a measure of analyte in the sample.

In many cases, however, the sacs including the detectable marker do not possess sufficient stability in that the detectable marker "leaks" from the sacs prior to or during the assay, which limits the effectiveness of such sacs in an assay. The term "leaks", as used herein, means that either the material escapes from an intact sac or the material escapes as a result of destruction of the sac.

In attempting to use absorbing dyes in a sac, in addition to the problem caused by leakage of dye or destruction of the sac, the absorbing dyes did not provide a sufficient signal to be read on simple instrumentation with acceptable precision and accuracy.

As a result, there is a need for improved sacs including a detectable marker.

In accordance with one aspect of the present invention, there is provided a sac which includes an absorbing dye which has an extinction coefficient which is at least 100,000, as measured in water. In addition, the dye is one which is soluble in water in a concentration of at least 0.1 M.

The dye which is included as a detectable marker in the sac is also a dye which has a net charge, either a net negative or a net positive charge, preferably a net negative charge. The charge of the dye is preferably identical to the charge of the material forming the sac in that such identical charge aids in preventing leakage from the sac. In addition, the dye is preferably one which is completely ionized at a pH of 5 to 9.

Applicant has found that an absorbing dye having such characteristics provides increased stability in that the dye does not tend to leak from the interior of the sac. Moreover, when used in an assay for an analyte, a sac containing such a dye provides for improved sensitivity in the assay.

In accordance with a particularly preferred embodiment, the absorbing dye which is included within the interior of the sac is a sulforhodamine B dye, and in particular, sulforhodamine as either a free acid or salt, e.q., sodium, lithium, potassium, ammonium salt, etc.

In general, the dye is included in the sac in a concentration of at least 0.001 M and preferably at least, 0.05 M. The concentration of the dye in the sac does not exceed the solubility of the dye in water.

In accordance with another aspect of the present invention, a sac including an absorbing dye of the type hereinabove described is sensitized with a ligand, which is either an antigen, hapten or antibody.

In accordance with yet a further aspect of the present invention, a sac including an absorbing dye, as hereinabove described, is employed in an assay for an analyte. The sac including the absorbing dye may be employed with or without sensitization with a ligand, depending upon the particular assay procedure.

The sacs, which include an absorbing dye in the interior thereof, may be any one of a wide variety of sacs which are generally known in the art, including polymer microcapsules (for example, those made by coascervation or interfacial polymerization), or vesicles which may be prepared from a wide variety of materials, preferably prepared from lipids. When the vesicle includes a lipid, it is often referred to as a liposome; however, as known in the art, vesicles can be produced from amphiphilic components which are not lipids. As known in the art, liposomes can be prepared from a wide variety of lipids, including phospholipids, glycolipids, steroids, relatively long change alkyl esters; e.g., alkyl phosphates, fatty acid esters, e. g., lecithin, fatty amines and the like. A mixture of fatty materials may be employed such as a combination of neutral steroid, a charged amphiphile and a phospholipid. As illustrative examples of phospholipids there may be mentioned sphingomyelin, dipalmitoyl, lecithin, and the like. As representative steroids, there may be mentioned cholesterol, cholestanol, lanosterol, and the like. As representative examples of charged amphiphilic compounds, which generally contain from 12 to 30 carbon atoms, there may be mentioned mono- or dialkyl phosphate ester, quaternary ammonium salts, or an alkylamine; e.g., dicetyl phosphate, distearyl amine, dihexadecyl amine, dilauryl phosphate, dioctadecyl sulfonate, didodecyl dioctylammonium formide, and the like.

Vesicles may be prepared by any one of a wide variety of procedures. Thus, for example, a liposome may be prepared by a reverse emulsion technique, as described in U.S. Pat. No. 4,235,871, wherein there is provided a water-in-oil emulsion containing the materials for forming the vesicle (generally phospholipids), as well as the dye to be encapsulated in the vesicle, followed by evaporation of the solvent to produce a gel-like mixture which is converted to a vesicle by either agitation or addition of the gel-like mixture to water.

Another procedure for producing a sac containing an encapsulated material is described in U.S. Pat. application Ser. No. 650,200 filed on Sept. 13, 1984, and such procedure may also be employed for producing a sac containing an absorbing dye in accordance with the invention.

Further procedures for producing sacs containing encapsulated markers are also disclosed in U.S. Pat. No. 4,343,826 and P.C.T. International Publication No. W080/01515 and such procedures are applicable to the present invention.

Polymer microcapsules are produced by procedures known in the art, except that the solution in which the microcapsules are formed also includes an absorbing dye whereby the interior of the polymer microcapsule includes the dye. The preparation of such microcapsules is disclosed, for example, in *Microencapsulation*

*Process and Applications,* edited by Jan E. Vandegger (Plenum Press 1974).

As hereinabove indicated, the sacs which include an absorbing dye of the type hereinabove described may be sensitized with a ligand. The ligand is generally either an antigen, antibody or hapten and when sensitized, such sacs may be employed in an assay for an analyte. For example, the sacs may be sensitized with a ligand by coupling the ligand to the sacs by a variety of procedures, including covalent coupling, derivatization, activation and the like.

The sacs may be coupled to the ligand by the use of an appropriate coupling or spacer compound (one that does not destroy the immunoreactivity of the ligand). As known in the art, the coupling compound has two reactive functional groups, one of which functional groups is capable of reacting or being linked to a functional group of the ligand portion of the tracer, and the other of which is capable of reacting or being linked to a functional group on the sacs. For example, the spacer or coupling compound, which includes at least two reactive substituent groups, may contain either a carboxyl, isocyanate, isothiocyanate, amino, thiol, hydroxy, sulfonyl, carbonyl, etc., substituent group, which, as should be apparent, is dependent upon the functional group present in the ligand and sacs which are to be coupled to each other.

Alternatively, the sacs may be coupled directly to the ligand. Thus, for example, if the ligand portion of the tracer has an amino substituent group, and the sac portion of the tracer has a carbonyl or carboxyl substituent group, then the ligand and sacs may be directly conjugated to each other by procedures known in the art; for example, an active ester technique.

The sacs may be sensitized with the ligand by either coupling the ligand to one of the materials to be used in forming the sacs or by coupling the ligand to the sacs after they are formed. Such procedures are generally known in the art, and no further details in this respect are deemed necessary for a complete understanding of the invention.

As hereinabove indicated, the sac containing an absorbing dye of the type hereinabove described may be employed in an assay for determining an analyte in a sample. The sac may or may not be derivatized with a ligand.

In the case where the sac is derivatized with a ligand for use in determining an analyte in a sample, the derivatized sac is generally referred to in the art as a "tracer". The ligand which is employed for derivatizing the sac is dependent upon the analyte to be determined. Thus, for example, if the assay is a competitive assay for determining an antigen or hapten, the ligand employed in producing the tracer is either the analyte or appropriate analog thereof. (The term "appropriate analog" means that the analog of the analyte is bound by the binder for the analyte.)

If the assay is a "sandwich" type of assay, then the ligand employed in producing the tracer would be a ligand which is specific for the analyte to be assayed; for example, an antibody elicited in response to the antibody or antigen to be assayed.

Thus, as should be apparent, the ligand which is employed for producing the tracer may be either an antigen, a hapten or an antibody.

The binder which is used in the assay is also dependent upon the analyte. Thus, for example, if the analyte is an antigen or hapten, the binder may be an antibody or a naturally occurring substance which is specific for the analyte. If the analyte is an antibody, the binder may be either an antibody, an antigen or naturally occurring substance which is specific for the analyte.

The binder which is used in the assay may be employed in supported or unsupported form. If supported, the binder may be supported on a wide variety of materials which are generally known to be suitable as supports for a binder in an assay. As representative examples of such materials, there may be mentioned polymers, glass particles, bacterial cells, etc. The solid support may be in a wide variety of forms, including sheet form, tube form, as a card or test strip, etc.

Thus, in accordance with another aspect of the present invention, there is provided an assay for an analyte in a sample which employs a binder and tracer wherein the binder binds at least the analyte, and the tracer is bound by one of the analyte and binder to provide in the assay free and bound tracer fractions. In the assay, a sac including an absorbing dye of the type hereinabove described is the source of the detectable marker in the assay.

In accordance with a representative assay, a sample containing or suspected of containing the analyte is incubated with a tracer, which is the analyte or appropriate analog thereof coupled to sacs including an absorbing dye as a detectable marker, in particular, sulforhodamine B or salt thereof, and a binder (specific for both the analyte and (tracer) with the binder preferably being supported on a solid support. The incubation results in competition between the tracer and analyte for binding sites on the binder, with the amount of tracer which is bound to the binder being inversely proportional to the amount of analyte in the sample.

The incubation is effected under conditions which prevent premature rupturing of the sacs. This portion of the assay is generally run in an appropriately buffered aqueous medium which is isotonic with the osmolarity of the sacs. Thus, conditions of temperature, pH and ionic concentration are controlled to prevent premature rupturing of the sacs. Thus, for example, an aqueous buffered medium is provided which is isotonic with the osmolarity of the sacs. In general, the buffer provides a pH in the order of from 5 to 9.

After separation of the bound and free tracer fractions, the dye may be released from either the bound and/or free fraction by lysing the sac by procedures known in the art; for example, use of a detergent or enzymatic lysing agent for lysing vesicles. The amount of absorbing dye which is released may be then measured for determining analyte in the sample. Thus, as generally practiced in the art, the value obtained for the assay is compared to values obtained by using an identical procedure using known amounts of analyte (standard analytes having known concentrations), which is employed for formulating a standard curve which may be employed for determining unknown quantities of analyte in a sample.

The tracer formed from a sac including an absorbing dye of the type hereinabove described, which is sensitized with a ligand, may also be employed in an assay for determining an analyte in a sample without lysing of the sac to release the dye. Such an assay is described in U.S. Pat. application Ser. No. 579,667, which was filed on Feb. 14, 1984. In accordance with such a procedure, a binder for at least one of the analyte and tracer is supported on a test area located on the surface of a solid support wherein the binder is supported on a test area of the solid support in a concentration whereby the tracer used in the assay, when bound to the binder or to the analyte bound to the binder, under assay conditions, is visible on the support, without further treatment. As described in such application, a preferred solid support is a cellulose ester with nitrocellulose giving exceptionally good results.

As described in such application, the binder which is supported on the solid support is either a binder for both the analyte and tracer, or a binder for only one of the analyte and tracer, with the type of binder which is employed being dependent upon the assay which is to be used for determining the analyte.

In one such technique, the binder which is supported on the solid support in an appropriate concentration is initially contacted with analyte; for example, antigen. Subsequently, the antigen bound to the binder on the solid support is contacted with tracer, which tracer is a sac including an absorbing dye of the type hereinabove described (in particular, sulforhodamine B or a salt thereof), with the sac being sensitized with an antibody to the analyte. The amount of tracer which is bound to the binder on the solid support through the analyte is directly proportional to the amount of analyte in the sample and the presence and/or amount of analyte present in the sample may be determined from the presence and/or amount of tracer which becomes bound to the support through the analyte. In accordance with this procedure, it is possible to visually determine the amount of tracer and or the presence of tracer without lysing of the sac.

In some cases, it may be possible to employ a sac including an absorbing dye of the type hereinabove described in an assay for an analyte, without derivatizing the sac. Thus, for example, in one type of assay, an analyte in a sample is incubated with a binder for the analyte supported on a solid support, and a tracer which is the analyte or appropriate analog thereof derivatized with an enzyme lysing agent. The tracer and analyte compete for binding sites on the binder, and after separating bound and free portions thereof, the bound and/or free portions may be contacted with a vesicle including an absorbing dye of the type hereinabove described, with the rate of release of marker from the sac, and/or amount of marker released from the sac being dependent upon the amount of tracer in the bound and/or free fraction. As generally practiced in the art, a standard curve may be prepared by repeating the assay with known quantities of analyte.

Thus, as should be apparent, the sac which includes an absorbing dye of the type hereinabove described may be employed in a variety of assays, and such sac may be employed in the assay with or without derivatization with a ligand.

The assays may be effected in a wide variety of samples. In most cases, the assay is effected in a sample of body fluid, such as, serum, urine, sputum, etc.

The assay may be employed for determining a wide variety of analytes. As representative examples of the types of analytes, there may be mentioned: drugs, including therapeutic drugs and drugs of abuse; hormones, vitamins; proteins, including antibodies of all classes; peptides; steroids; bacteria; fungi; viruses; parasites; components or products of bacteria, fungi, viruses or parasites; allergens of all types; products or components of normal or malignant cells; etc. As particular examples, there may be mentioned $T_4$; $T_3$; digoxin; hCG; insulin; theophylline; antibiotics, such as gentamicin and tobramycin; anticonvulsants, such as phenobarbital, carbamezapine, valproic acid, antiarrythmics, such as lidocaine, quinidine; etc.

Thus, in accordance with the present invention, there is provided a sac, and in particular, a vesicle or liposome, which includes an absorbing dye having specific characteristics, with the absorbing dye preferably being sulforhodamine B or salt thereof, and such sac may or may not be derivatized with a ligand; in particular, an antigen, hapten or antibody. The sac when derivatized with a ligand is particularly useful as a tracer in an assay for an analyte in a sample.

Although the dye used in the sac is an absorbing dye, such dyes also have fluorescent properties. Accordingly, within the scope of the invention, such absorbing dyes may be detected by fluorescence rather than by absorption characteristics.

The present invention will be further described with respect to the following example; however, the scope of the invention is not to be limited thereby:

EXAMPLE I

LIPOSOME PREPARATION

1. To a 100 ml round-bottom rotoevaporator flask, add the following:
   a. 48 mg. cholesterol, Sigma,#CH-S.
   b. 104 mg distearoyl phosphatidyl choline (DSPC), Avanti Polar Lipids #850365 (20 mg/ml in $CHCl_3$)
   c. 3.75 mg crosslink agent (distearoyl phosphatidyl ethanol-amine-(p-maleimidophenyl) butyrate (DSPE-MPB) prepared in-house, 2 mg/ml in $CHCl_3$ as described in Example IA)
   d. 6.0 ml isopropyl ether, Fisher #E-141
   e I.0 ml methanol, Aldrich #15, 490-3
2. Swirl to mix.
3. Add 5.0 ml 0.1 M Sulforhodamine B, Eastman #14321, prepared in 0.1 M sodium acetate/0.1 M NaCl, pH 4.5 buffer.
4. Swirl to mix.
5. Flush vessel with $N_2$.
6. Sonicate in room temperature, water bath sonicator for 10 minutes in order to emulsify.
7. Place on rotoevaporator with the following settings:
   Water Bath Temperature =44° C.
   Rotation Speed =4
8. Slowly increase vacuum until foaming ceases (approximately 30 –40 min.)
9. Reduce pressure and allow liposomes to anneal at 44° C. for 30 min.
10. Add 10 ml of warm (50–52° C.) 0.1 molar sulforhodamine B to vessel and mix.
11. Extrude the warm liposome preparation through a 0.4 micron, then a 0.2 micron Bio-Rad Unipore polycarbonate membrane (Bio-Rad #313-0059 and #313-5059, respectively).
12. Dilute liposomes to a total volume of approximately 80 ml in a 90 ml ultracentrifuge tube using sodium acetate/ saline buffer, pH 4.5.
13. Centrifuge at 75,000 Xg for 30 min.
14. Resuspend pelleted liposomes to 80 ml with sodium acetate/ saline buffer, pH 4.5.
15. Repeat #13 and #14, then #13 again.
16. Resuspend pelleted liposomes in 10 ml Tris buffer, pH 8.0 (50 mM Tris, 100 mM NaCl, 1 mM EDTA, 310 mOs/kg).
17. Hold at 4oC until protein reaction.

EXAMPLE IA

PREPARATION OF DISTEAROYLPHOSPHATIDYLETHANOLAMINE MALEIMIDOPHENYLBUTYRATE USED IN EXAMPLE I

Distearoylphosphatidylethanolamine (119.2 mg, 0.1593 mmol, Avanti Polar Lipid) was suspended in 30 ml of chloroform and heated to reflux under a nitrogen atmosphere until all solid had dissolved. The solution was allowed to cool to room temperature followed by the addition of triethylamine (22.2 ul, 0.1593 mmol, Aldrich) and succinimidyl-4-(p-maleimidophenyl) butyrate (79.45 mg, 0.2230 mmol, Pierce). The reaction mixture was allowed to stir overnight at room temperature under a nitrogen atmosphere. The mixture was concentrated under reduced pressure to yield a pale yellow waxy solid (270.7 mg) that appeared as one major spot and several minor spots upon tlc analysis (silica, 65:25:4 $CH_2Cl_2:CH_3OH:H_2O$). The spot was visualized with UV light and Molybdenum Blue Spray Reagent (Sigma), $R_f$ 0.5. The crude product was chromatographed on four silica gel, preparative, thick-layer plates (E. Merck, 2.0 mm) developing with 65:25:4 $CH_2Cl_2:CH_3OH:H_2O$. The upper band of the two Molybdenum Blue active bands was isolated and the product extracted with 50% $CH_2Cl_2:C_2H_5OH$. Evaporation of the solvent afforded the product as a white solid (65.75 mg). IR (Neat): 2910(s), 2845(s), 1734(s), 1715(s), 1510(m), 1460(m), 1390(m), 1370(mw), 1242(m), 1230(m), 1100(m), 1060(m), (m), 820(m), 685 $cm^{-1}$(m). The liposomes prepared in this manner include rhodamine dye and may be sensitized with a ligand by procedures known in the art to produce a tracer for use in the present invention.

SENSITIZING LIPOSOME (EXAMPLE I) WITH ANTIBODY TO PRODUCE TRACER

EXAMPLE II

1. To 8 mg. protein A purified antibody, add 0.4 ml 1 M dithiothreitol in sodium acetate/saline buffer, pH 4.5.
2. Vortex and let react 30 min. at room temperature in the dark.
3. Remove dithiothreitol by passing the reaction volume over a Sephadex G-25 medium column equilibrated with Tris pH 8.0 buffer (50 mM Tris, 100 mM saline, 1 mM EDTA, 310 mOs/ kg).
4. Monitor the O.D. 280 and pool void volume fractions.
5. Mix this solution with the 10 ml of freshly prepared liposomes.
6. Flush with $N_2$ and seal.
7. React overnight at room temperature.
8. Wash twice, by centrifugation, these protein-labeled liposomes using the standard Tris buffer.
9. After last wash, resuspend pellet in 40 ml Tris.
10. Store at 4° C.

EXAMPLE III

NITROCELLULOSE DISC IMMUNOASSAY FOR HCG (PREGNANCY TEST)

REAGENTS

1. Adsorption Buffer 5: BD, Catalog #614335.
2. HCG antibody to the alpha-chain of hcG.
3. Nitrocellulose Paper: Schliecher & Schuill, ME 25, 0.45 um porosity.
4. Bovine Serum Albumin: Sigma, Catalog #A-7906.
5. Urine Controls: BDI, Catalog #255815.
6. Tracer: Liposome prepared by method of Example I and sensitized with antibody to the chain of hcG by the method of Example II.

PROCEDURE

1. Cut 1cm disc of nitrocellulose paper.
2. Pipet 3 ul of 1:50 dilution of HCG antibody (dilution made in AB5) to the center of disc.
3. Allow to dry at room temperature 15 minutes.
4. Pipet 300 ul of 5% BSA in AB5 (filtered through 0.45 micron filter prior to use) to each disc.
5. Incubate disc 1 hour at 37° C.
6. Decant liquid.
7. Pipet 200 ul of urine control or urine.
8. Incubate 1 hour at room temperature.
9. Decant control or urine.
10. Wash disc twice with 1.5 ml AB5.
11. Pipet 300 ul of 1:12 dilution of tracer (dilution made in AB5) to each disc (stock liposomes contain about 1 u mole. lipid/ml).
12. Incubate 1 hour at room temperature.
13. Decant tracer.
14. Wash twice with 1.5 ml AB5.
15. Visible spot is positive for pregnancy.

| \multicolumn{4}{c}{QUALITATIVE URINE RIA RESULTS vs. NITROCELLULOSE DISC TEST RESULTS} |
|---|---|---|---|
| Urine Number | Gestation Period | RIA Results | Spot Test |
| 1 | 11 wk | Pos | Pos |
| 2 | 10 wk | Pos | Pos |
| 3 | 7½ wk | Pos | Pos |
| 4 | 8½ wk | Pos | Pos |
| 5 | 11¼ wk | Pos | Pos |
| 6 | 11½ wk | Pos | Pos |
| 7 | 9 wk | Pos | Pos |
| 8 | 8½ wk | Pos | Pos |
| 9 | 10 wk | Pos | Pos |
| 10 | 8½-12 wk | Pos | Pos |
| 11 | None | Borderline | Neg |
| 12 | None | Neg | Neg |
| 13 | None | Neg | Neg |
| 14 | None | Neg | Neg |

RIA done by BD HCG $I^{125}$ kit.

EXAMPLE IV

PREPARATION OF DISTEAROYLPHOSPHATIDYLETHANOLAMINE-DIGOXIGENIN

Distearoylphosphatidylethanolamine (400.0 mg, 0.5346 mmol, Avanti Polar Lipid) was suspended in 50 ml of $CHCl_3:CH_3OH$ (9:1) and heated to reflux under a nitrogen atmosphere until all solid had dissolved. The solution was allowed to cool followed by the addition of 3-ketodigoxigenin (207.7 mg, 0.5346 mmol) and 2.0 g of 4A sieves (Sigma). The reaction mixture was allowed to stir at 60oC for 3 hr. under a nitrogen atmosphere at which time sodium cyanoborohydride (36.95 mg, 0.5881 mmol, Sigma) was added. The mixture was then allowed to stir at room temperature overnight. The reaction was filtered and concentrated under reduced pressure to yield a white foam (579.6 mg) that appeared as one major spot and several minor spots under tlc analysis (silica, 20% $CH_3OH:CH_2Cl_2$). The spot was visualized by Phosphomolybdic Acid Spray Reagent (Sigma), $R_f$ 0.3.

The crude product was purified by low pressure column chromatography (silica gel, 10% CH$_3$OH—CH$_2$Cl$_2$) to yield the product as a white solid (185.3 mg). The product was detected by a variable wavelength UV detector set at 230 nm.

EXAMPLE V

PREPARATION OF LIPOSOME CONTAINING SULFORHODAMINE B SENSITIZED WITH DIGOXIGENIN (TRACER)

Phosphatidyl choline, dipalmitoyl (dppc), cholesterol (chol), phosphatidyl ethanolamine, distearoyl-digoxigenin (dspe-dig) (Example IV), and phosphatidyl glycerol, dipalmitoyl (dppG) are dissolved in chloroform/methanol (20:1) in the ratio of 50 mole % chol, 40 mole % dppc, 10 mole % dppg and a trace amount (e.g., 200 ug) of dspe-dig is added. The lipids are dried on the inside of a round bottom flask under reduced pressure on a rotary evaporator, and subsequently placed on a lyophilizer overnight to remove all traces of residual solvent. A solution of 0.1M sulforhodamine B in water is added to the flask (10 ml), and the flask is shaken vigorously or, if desired, sonicated briefly. This operation is conducted at 60° C. The liposomes form spontaneously under this condition as is known in the art, and contain approximately 0.1M rhodamine dye encapsulated. Detectable digoxigenin is exposed on the surface of the liposomes. The liposomes are washed several times in a buffer solution of the same osmolarity as the encapsulated dye (about 310 mosm/Kg) to prevent osmotic lysis. The preparation is filtered through a 0.4 or 0.2u filter to remove the larger liposomes. The liposomes are diluted in buffer solution so as to contain 1u mole of phospholipid per ml of buffer solution.

EXAMPLE VI

DIGOXIN PROCEDURE

Paper Spotting Procedure:

1. Spot nitrocellulose paper (ME-25) dots with 5 ul of rabbit anti-digoxin antibody in Tris buffer containing 0.1% BSA, (6.005 gm Tris base, 0.358 gm EDTA trisodium, 6.83 gm NaCl, 0.2 gm NaN$_3$, 1 gm BSA q.s. to 1 L with HPLC water, pH to 8.0 with HCl. Adjust to 310 mOs/kg using a 4 M NaCl solution at various concentrations which demonstrate inhibition. Let air dry for 30 minutes.

2. Cover the nitrocellulose paper dots with 300 ul of 3% BSA in Tris buffer (6.055 gm Tris base, 0.358 gm EDTA trisodium, 6.83 gm NaCl, 0.2 gm NaN$_3$, 30 gm BSA q.s. to 1 liter with HPLC water, pH to 8.0 with HCl. Adjust to 310 mOs/kg using 4 M NaCl solution. Let dots soak in BSA for 30 min to 1 hr or until the dot is completely saturated. After saturation, remove BSA either by decantation or by aspiration.

Assay Procedure:

1. Cover pretreated dots with digoxin standards (0 ng/ml; 0.5 ng/ml; 1.0 ng/ml; 2.5 ng/ml) and/or patient serums. Let dot soak in standards and/or serums for 10 minutes. Remove standards and/or patient serums by either decantation or aspiration. After removing standards and/or patient serums, wash dots twice with Tris buffer (6.005 gm Tris base, 0.358 gm EDTA trisodium, 6.83, gm NaCl, 0.2 gm NaN3, q.s. to 1 liter with HPLC water, pH to 8.0 with HCl. Adjust to 310 mOs/kg using NaCl solution.

2. Cover dots with 500 ul of sensitized liposomes (containing 100-400 ug PE-digoxigenin of Example VI which have been diluted in Tris buffer (6.055 gm Tris base, 0.358 gm EDTA trisodium 6.83 gm NaCl, 0.2 gm NaN$_3$, q.s. to 1 L with HPLC water, pH to 8.0 with HCl. Adjust to 310 mOs/kg using 4 M NaCl solution at a dilution that demonstrates inhibition. Let dot soak in the liposomes for 15 minutes. Remove liposomes by either decantation or aspiration. After removing liposomes, wash dots tWice with Tris buffer (6.055 gm Tris base, 0.358 gm EDTA trisodium, 6.83 gm NaCl, 0.2 gm NaN$_3$ q.s. to 1 L with HPLC water, pH to 8.0 with HCl. Adjust to 310 mOs/kg using 4M NaCl solution.

Assay Interpretation:

1. For the purposes of this study, the antibody dilutions used were 1:200, 1:1200, and 1:2200. These dilutions may vary. The results are as follows:

At the 1:200 dilution pink dots were obtained at all standard concentrations. This dilution is used as a reference only.

At the 1:1200 dilution pink dots were obtained at the 0 ng/mn, 0.5 ng/ml, and 1.0 ng/ml standard concentrations. There was no pink dot at the 2.5 ng/ml standard concentration showing that when 2.5 ng/ml of digoxin or higher is present, no color would be visible.

At the 1:2200 dilution pink dots were obtained at the 0 ng/ml, 0.5 ng/ml standard concentrations. There were no pink dots at the 1.0 ng/ml and 2.5 ng/ml standard concentrations showing that when 1.0 ng/ml of digoxin or higher is present, no color would be visible.

For Patient Serum Determinations:

Ten patient serums were set up as previously described, and the results were compared to the following key:

| | Color | No Color |
|---|---|---|
| At the 1:200 Dilution: | If patient serum is less than 2.5 ng/ml | If patient serum is greater than 2.5 ng/ml |
| At the 1:2200 Dilution: | If patient serum is less than 1.0 ng/ml | If patient serum is greater than 1.0 ng/ml |

Using this format, nine out of ten patient serum value ranges (i.e., greater than 2.5 ng/ml, within 1.0-2.5 ng/ml range; or less than 1.0 ng/ml) were determined accurately.

EXAMPLE VII 132 umoles cholesterol, 113 umoles distearolyphosphatidylcholine, 13.2 umoles distearoylphosphatidylglycerol, and 200 ugram distearoylophosphatidylethanolamine-digoxigenin conjugate were dissolved in 20 ml chloroform-methanol (9:1 v/v). The mixture was dried in a 250 ml size round bottom flask using a rotary evaporator at 37° C. The dried lipid film was further dried in-vacuo at 25° C. for 16 hours and swollen in 2.7% (w/v) glycerol solution containing 1 mM EDTA and 0.02% NaN$_3$ at pH 6.7. Swelling was achieved by gentle swirling at 60° C. for 3 minutes. The turbid liposome suspension was spun for 10 minutes at 2000 rpm to sediment large multilamellar vesicles, and the supernatant was collected and spun for 30 minutes at 30,000 rpm to sediment the large unilamellar vesicles. Loading the vesicles with dye was achieved by resuspending the empty liposome pellet in 20 ml of 0.1 M solution of sulforhodamine B at pH 6.7 and extruding the suspension sequentially through polycarbonate membranes of 1.0 u, 0.4 u, and 0.2 pore sizes. Thirty ml of buffer containing 20 mM Tris, 20 mM EDTA, 2% (w/v) glycerol, 0.05% DMSO,and 0.02% NaN$_3$ were added, and the liposomes were spun for 30 minutes at 30,000 rpm. The pellet was resuspended and washed twice in the same buffer to remove unencapsulated dye, and the washed loaded liposomes were diluted in the same buffer at 1 umole phospholipid phosphorus per ml.

The effectiveness of the liposomes as nonisotopic tracers in immunoassay for digoxin was tested by coating polypropylene 12 ×75 mm tubes with 1:2000 dilution of sheep anti-digoxin antiserum. The tubes were filled with 50 ul of the liposomes, 100 ul serum containing known amounts of digoxin as clinical samples, and 850 ul of Tris-saline buffer at pH 8.0 that also contained 0.1% bovine serum albumin, 1 mM EDTA, and 0.02% sodium azide. After 30 minutes incubation at 37° C., the tubes were emptied by aspiration and washed with Tris-saline buffer, 1 ml of 5% Triton X-100 was added to lyse the liposome bounds to the tube wall, and the absorbance as measured by 565 nm on a spectrometer. Absorbance at zero nanograms digoxin was 0.080 O.D., and the standard curve generated for digoxin was linear on a logit-log plot with 50% displacement of liposome binding at the dose of 2 ng digoxin per ml in serum. Clinical samples gave levels that correlated well with the levels determined by radio-immunoassay.

The present invention is particularly advantageous in that there is provided a sac which contains an absorbing dye whereby an assay may be accomplished by use of simple equipment, such as a colorimeter, or an inexpensive spectrophotometer. Applicant has surprisingly found that the absorbing dye should have certain characteristics in order to provide the requisite stability. In particular, applicant has tested other dyes such as fluorescein and derivatives thereof, and has found that such dyes, when incorporated into a sac, do not provide the requisite stability; i.e., the dyes significantly leaked from the sacs during storage and did not have sufficient sensitivity for determination by use of simple instrumentation.

The stability of the vesicles is excellent, and dye leakage has been found to be low over storage periods of six months at room temperature.

The amplification obtained with tracers produced in accordance with the invention (vesicles including sulforhodamine B sensitized with a ligand) is in the range of 1000 to 10,000 times that which can be achieved with one marker group attached to each tracer molecule. The assay can be effectively read colorimetrically on a simple spectrophotometer. The precision and accuracy of the assay compares favorably with radioimmunoassays, and is superior to results obtained with manual enzyme immunoassays.

These and other advantages should be apparent to those skilled in the art from the teachings herein.

Numerous modifications and variations of the present invention are possible in light of the above teachings; therefore, within the scope of the appended claims, the invention may be practiced otherwise than as particularly described.

What is claimed is:

1. A composition, comprising:
a sac, said sac including absorbing an dye having an extinction coefficient of at least 100,000, said dye being soluble in water in a concentration of at least 0.1 M.

2. The composition of claim 1 wherein the dye has a net charge.

3. The composition of claim 2 wherein the dye is completely ionized in water at a pH of from 5 to 9.

4. The composition of claim 2 wherein the sac includes the dye in a concentration of at least 0.01 M.

5. The composition of claim 4 wherein the sac includes the dye in a concentration of at least 0.05 M.

6. The composition of claim 1 wherein the sac is sensitized with a ligand selected from the group consisting of antigens, antibodies and haptens.

7. The composition of claim 6 wherein the dye has a net charge, and the sac is a vesicle.

8. The composition of claim 7 wherein the dye is completely ionized in water at a pH of from 5 to 9.

9. The composition of claim 8 wherein the sac includes the dye in a concentration of at least 0.05 M.

10. A composition, comprising:
a sac, said sac including a sulforhodamine dye.

11. In an assay for an analyte in a sample wherein a sac employing a detectable marker is employed as a measure of analyte, the improvement comprising:
detecting, as a measure of analyte, a sulforhodamine dye present in a sac as defined in claim 10.

12. The assay of claim 11 wherein the sac is sensitized with a ligand selected from the group consisting of antigens, antibodies and haptens.

13. The assay of claim 12 wherein the absorbing dye present in the sac is detected after release from the sac.

14. The composition of claim 10 wherein the absorbing dye is selected from the group consisting of sulforhodamine B and salts thereof.

15. The composition of claim 14 wherein the sac includes the dye in a concentration of at least 0.01 M, and the sac is a vesicle.

16. The composition of claim 15 wherein the sac includes the dye in a concentration of at least 0.05 M.

17. The composition of claim 14 wherein the sac is sensitized with a ligand selected from the group consisting of antigens, antibodies and haptens.

18. The composition of claim 17 wherein the sac includes the dye in a concentration of at least 0.05 M, and the sac is a vesicle.

19. In an assay for an analyte in a sample wherein a sac employing a detectable marker is employed as a measure of analyte, the improvement comprising:
detecting, as a measure of analyte, an absorbing dye present in a sac, said absorbing dye having an extinction coefficient of at least 100,000, and said absorbing dye being soluble in water in a concentration of at least 0.1 M.

20. The assay of claim 19 wherein the absorbing dye present in the sac is detected after release from the sac.

21. The assay of claim 19 wherein the sac is sensitized with a ligand selected from the group consisting of antigens, antibodies and haptens.

* * * * *